US010357061B2

(12) United States Patent
Li et al.

(10) Patent No.: US 10,357,061 B2
(45) Date of Patent: Jul. 23, 2019

(54) ELECTRONIC CIGARETTE HAVING PROTECTION FOR A SUCTION NOZZLE

(71) Applicant: SHENZHEN FIRST UNION TECHNOLOGY CO., LTD., Shenzhen (CN)

(72) Inventors: Yonghai Li, Shenzhen (CN); Zhongli Xu, Shenzhen (CN); Huiyong Yan, Shenzhen (CN)

(73) Assignee: SHENZHEN FIRST UNION TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 15/713,743

(22) Filed: Sep. 25, 2017

(65) Prior Publication Data

US 2018/0084832 A1  Mar. 29, 2018

(30) Foreign Application Priority Data

Sep. 26, 2016 (CN) .......................... 2016 2 1082925

(51) Int. Cl.
| A24F 1/10 | (2006.01) |
| A24F 47/00 | (2006.01) |
| A61M 15/00 | (2006.01) |
| A61M 15/06 | (2006.01) |
| B05B 12/08 | (2006.01) |
| B05B 17/06 | (2006.01) |

(52) U.S. Cl.
CPC ....... *A24F 47/008* (2013.01); *A61M 15/0023* (2014.02); *A61M 15/06* (2013.01); *B05B 12/081* (2013.01); *B05B 17/0615* (2013.01); *A61M 2205/11* (2013.01); *A61M 2209/086* (2013.01)

(58) Field of Classification Search
CPC .............................. A24F 47/008; A24F 47/002
USPC .................................................... 131/328–330
See application file for complete search history.

(56) References Cited

U.S. PATENT DOCUMENTS

| 9,271,526 B2* | 3/2016 | Liu ......................... A24F 15/12 |
| 9,936,733 B2* | 4/2018 | Ampolini .............. A24F 47/008 |
| 9,936,735 B1* | 4/2018 | Shotey .................. A24F 47/008 |
| 10,058,122 B2* | 8/2018 | Steingraber .......... A24F 47/008 |

(Continued)

FOREIGN PATENT DOCUMENTS

| CN | 203388273 U | 1/2014 |
| CN | 203492784 U | 3/2014 |

OTHER PUBLICATIONS

European Search Report.

*Primary Examiner* — Hae Moon Hyeon
(74) *Attorney, Agent, or Firm* — IPro, PLLC; Na Xu

(57) ABSTRACT

An electronic cigarette includes a housing, a sleeve, an atomizer, a latch assembly and a control assembly. The sleeve includes a first limiting position and a second limiting position. The atomizer includes a mouthpiece. The atomizer is capable of being inserted into the sleeve and telescoping relative to the sleeve along an axial direction of the sleeve, so as to expose the mouthpiece or take out the atomizer from the sleeve. The latch assembly is arranged on an end of the atomizer opposite to the mouthpiece and configured to latch the atomizer in the sleeve when the atomizer is retracted into the sleeve and is positioned at the first limiting position. The control assembly is arranged on the sleeve and configured to unlock the latch assembly to allow the end of the atomizer to move to the second limiting position along the axial direction of the sleeve.

9 Claims, 2 Drawing Sheets

(56) References Cited

U.S. PATENT DOCUMENTS

| | | | |
|---|---|---|---|
| 2007/0045288 A1 | 3/2007 | Nelson | |
| 2012/0255546 A1* | 10/2012 | Goetz | A61M 11/041 128/202.21 |
| 2013/0042865 A1 | 2/2013 | Monsees et al. | |
| 2015/0245666 A1* | 9/2015 | Memari | A24F 15/12 131/329 |
| 2016/0050975 A1* | 2/2016 | Worm | A24F 47/008 131/328 |
| 2016/0295919 A1* | 10/2016 | Thomas, Jr. | A24F 47/008 |
| 2017/0099877 A1* | 4/2017 | Worm | A61M 11/042 |
| 2018/0199630 A1* | 7/2018 | Qiu | A24F 47/008 |

* cited by examiner

ELECTRONIC CIGARETTE HAVING PROTECTION FOR A SUCTION NOZZLE

CROSS-REFERENCE TO RELATED APPLICATIONS

The present disclosure claims priority to Chinese Patent Application No. 201621082379.6, filed with the Chinese Patent Office on Sep. 26, 2016, titled "ELECTRONIC CIGARETTE," the entire contents of which are incorporated herein by reference.

TECHNICAL FIELD

The present disclosure relates to the technical field of electronic cigarettes, and in particular, relates to an electronic cigarette.

BACKGROUND

In current market, suction nozzles of atomizers of electronic cigarettes are fixed. The suction nozzles of the atomizers are always exposed outside, which is unsanitary in use. Protection for the suction nozzles of the atomizers depends on package boxes, and thus the atomizers are inconvenient to carry and use.

SUMMARY

An embodiment of the present disclosure provides an electronic cigarette. The electronic cigarette includes:

a housing;

a sleeve received in the housing, the sleeve including a first limiting position and a second limiting position;

an atomizer including a mouthpiece, the atomizer capable of being inserted into the sleeve and telescoping relative to the sleeve along an axial direction of the sleeve, so as to expose the mouthpiece or take out the atomizer from the sleeve;

a latch assembly arranged on an end of the atomizer opposite to the mouthpiece, the latch assembly configured to latch the atomizer in the sleeve when the atomizer is retracted into the sleeve and is positioned at the first limiting position; and a control assembly arranged on the sleeve, the control assembly configured to unlock the latch assembly to allow the end of the atomizer to move to the second limiting position along the axial direction of the sleeve.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed.

DETAILED DESCRIPTION

To make a person skilled in the art better understand the present disclosure, the technical solutions of this disclosure are further described with reference to the accompanying drawings and the specific embodiments of the present disclosure.

Figure 1:
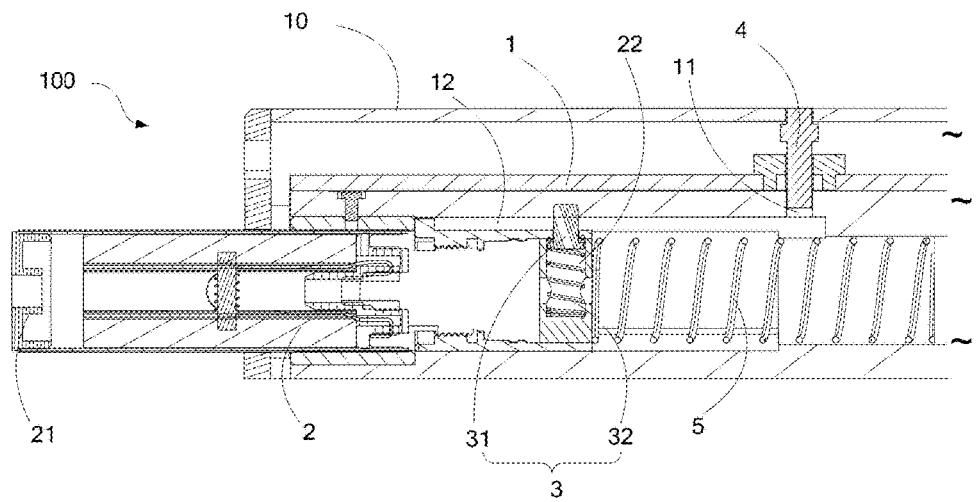
FIG. 1 is a schematic partial cross-section view of an electronic cigarette in a first operation state according to a first embodiment of the present disclosure.
Figure 2:
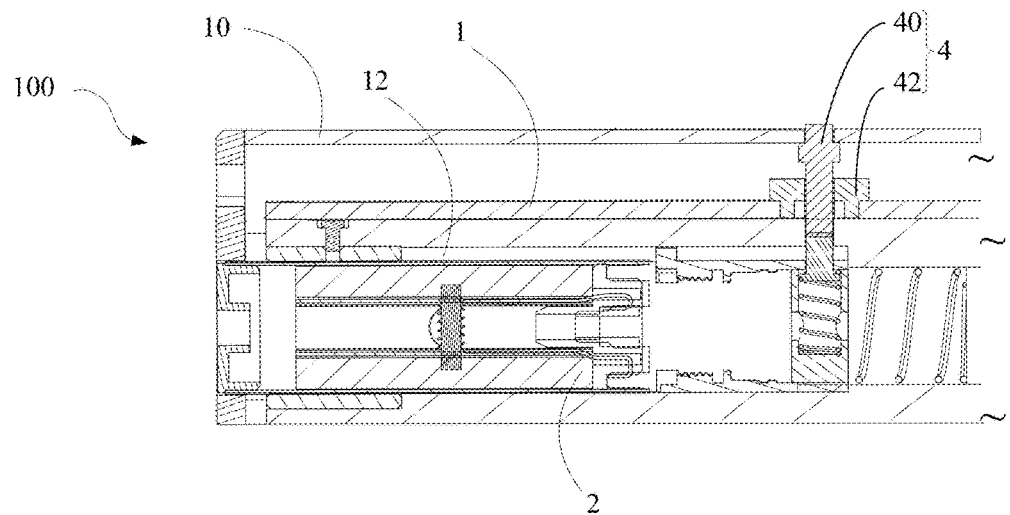
FIG. 2 is a schematic partial cross-section view of the electronic cigarette of FIG. 1 in a second operation state.

FIG. 1 and FIG. 2 illustrate an electronic cigarette 100 according to a first embodiment of the present disclosure. The electronic cigarette 100 includes a housing 10, a sleeve 1 arranged in the housing 10, an atomizer 2 including a mouthpiece 21 (also referred to as a suction nozzle), a latch assembly 3 and a control assembly 4. The sleeve 1 has a first limiting position (not labeled) and a second limiting position (not labeled). The atomizer 2 is capable of being inserted into the sleeve 1, and capable of telescoping along an axial direction of the sleeve 1 relative to the sleeve 1 to expose the mouthpiece 21 or take out the atomizer 2. The latch assembly 3 is arranged on one end of the atomizer 2 opposite to the mouthpiece 21, and is configured to latch the atomizer 2 in the sleeve 1 when the atomizer 2 is retracted into the sleeve 1 and is defined to the first limiting position; and the control assembly 4 is arranged on the sleeve 1, and is configured to unlock the latch assembly 3 to allow the other end of the atomizer 2 to move to the second limiting position along the axial direction of the sleeve 1. In this illustrated embodiment, the atomizer 2 is movable relative to sleeve 1, such that the mouthpiece 21 arranged on the atomizer 2 is non-fixed. When being not smoked, the mouthpiece 21 arranged on the atomizer 2 may be retracted into the sleeve 1, and when being smoked, the mouthpiece 21 arranged on the atomizer 2 may stretch out of the sleeve 1, which is easy to carry, and is sanitary for use.

It should be noted that, to implement the function of the electronic cigarette, an electronic core module is arranged in the housing 10, and connected to the atomizer 2. The specific connection line is not illustrated in the drawings, and is not defined in the present disclosure. The electronic core module includes a battery and a controller, wherein the battery may be arranged on a bottom of the sleeve 1, and the controller may be arranged on one side of the housing 10 opposite to the sleeve 1, and the controller is further provided with a simulated smoking butt on the side of the housing 10. In this case, a shape of the housing 10 may be variable, which is not defined. Since any electronic core module and simulated smoking butt and any combinations may be used in the present disclosure to implement the electronic cigarette of the present disclosure, the controller of the electronic core module and the simulated smoking butt are not defined in the present disclosure, and the implementation is not descried herein any further. In addition, a specific structure of the atomizer 2 is not defined in the present disclosure, the electronic cigarette of the present disclosure may be implemented in any manner, which includes an atomizing housing, a liquid guiding body received in the atomizing housing, and a heating wire wound on the liquid guiding body, wherein the heating wire is connected to the electrical core module to provide a heating source. The details are not given herein any further.

Further, referring to FIG. 1 and FIG. 2, the electronic cigarette 100 includes a first elastic assembly 5, wherein one end of the first elastic assembly 5 abuts against the other end of the atomizer 2 opposite to the mouthpiece 21, the other end of the first elastic assembly 5 is connected to a bottom of the sleeve 1, and the first elastic assembly 5 provides a thrust to push the atomizer 2 outwards along the axial direction of the sleeve 1 when the atomizer 2 is retracted into the sleeve 1. When the atomizer 2 is retracted into the sleeve 1, the first elastic assembly 5 is in a compressed state, and the first elastic assembly 5 in the compressed state provides a thrust to push the atomizer 2 outwards along the axial direction of the sleeve 1 under the effect of an elastic force, which enables the atomizer 2 to eject outwards, and thereby enables the mouthpiece 21 arranged on the atomizer 2 to stretch out of the sleeve 1. In this illustrated embodiment, the first elastic assembly 5 is a spring, and in other embodiments, the first elastic assembly 5 may also be other elastic parts, for example, an elastic piece.

In addition, in this illustrated embodiment, the latch assembly 3 is configured to latch the atomizer 2 into the sleeve 1 when the atomizer 2 is retracted into the first limiting position and when an outer end portion of the mouthpiece 21 is flushed with an outer end portion of the housing 10, such that when being not smoked, the appearance of the electronic cigarette 100 is beautiful.

Specifically, in this illustrated embodiment, referring to FIG. 1 and FIG. 2, the sleeve 1 defines a positioning hole 11 on an inner wall thereof, the positioning hole 11 are arranged in the first limiting position, and the latch assembly 3 includes a second elastic assembly 32 and a limiting pin 31. The second elastic assembly 32 elastically offsets the limiting pin 31 along a radial direction of the sleeve 1, such that when the other end of the atomizer 2 opposite to the mouthpiece 21 is retracted into the first limiting position, the limiting pin 31 is aligned with the positioning hole 11 and is further latched into the positioning hole 11. In this illustrated embodiment, the second elastic assembly 32 is a spring, and in other embodiments, the second elastic assembly 32 may be other elastic parts, for example, an elastic piece.

Further, in this illustrated embodiment, the other end of the atomizer 2 defines a receiving cabin 22, the second elastic assembly 32 and the limiting pin 31 are sequentially arranged in the receiving cabin 22 along the radial direction of the sleeve 1. In other embodiments, the other end of the atomizer 2 may define a circular hole, such that the second elastic assembly 32 and the limiting pin 31 are sequentially arranged in the circular hole along the radial direction of the sleeve 1.

In this illustrated embodiment, referring to FIG. 1 and FIG. 2, the control assembly 4 includes a control button 40, the control button 40 is arranged on the first limiting position, and partially exposed on an outer side of the sleeve 1, such that the limiting pin 31 is unlocked from the first limiting position by pressing the control button 40. The control assembly 4 further includes other components. For example, the control button 40 is movably connected to a connection member 42 of the sleeve 1. Further, in this illustrated embodiment, an outer side portion of the control button 40 exposed to the sleeve 1 is flushed with an outer surface of the housing 10, such that an entire appearance of the electronic cigarette 100 is beautiful.

Further, in this illustrated embodiment, the second limiting position is arranged on the inner wall of the sleeve 1, and is spaced apart from the first limiting position at a predetermined distance. In other embodiments, the second limiting position may be also arranged on an outer end of the sleeve 1.

Further, the inner wall of the sleeve 1 defines an axial limiting groove 12, the axial limiting groove 12 is communicated with the positioning hole 11, and is configured to limit the limiting pin 31 when the atomizer 2 telescopes relative to the sleeve 1 along the axial direction of the sleeve 1. The axial limiting groove 12 prevents the limiting pin 31 from deviation when the atomizer 2 telescopes along the axial direction of the sleeve 1, thereby resulting in that the latch assembly 3 fails to well latch the atomizer 2 into the sleeve 1.

Figure 3:
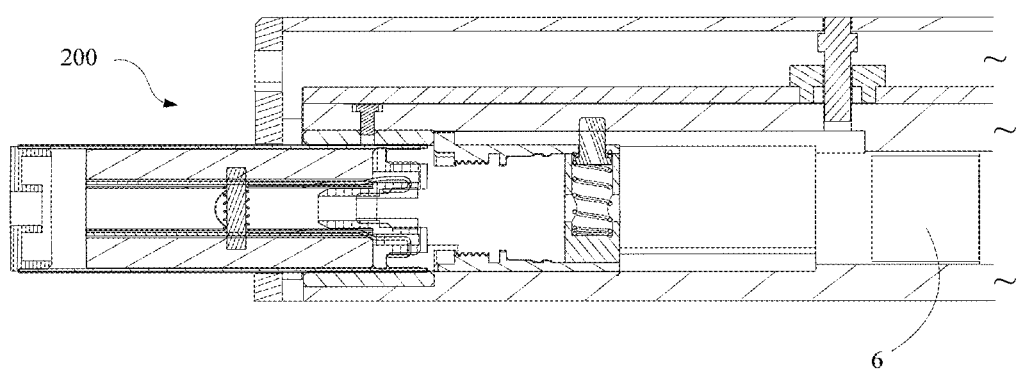
FIG. 3 is a schematic partial cross-section view of an electronic cigarette in a first operation state according to a second embodiment of the present disclosure.

FIG. 3 illustrates an electronic cigarette 200 according to a second embodiment of the present disclosure. The electronic cigarette 200 shown in FIG. 3 is similar to the electronic cigarette 100 shown in FIGS. 1 and 2, except that the electronic cigarette 200 further includes an air pump 6. The air pump 6 is arranged on a bottom of the sleeve 1, and configured to provide a thrust to push the atomizer 2 outwards along the axial direction of the sleeve 1 when the atomizer 2 is retracted into the sleeve 1. When the control assembly 4 unlocks the latch assembly 3, the air pump 6 is in an operation state and thus provides a thrust to push the atomizer 2 outwards, and pushes the other end of the atomizer 2 to the second limiting position.

Figure 4:
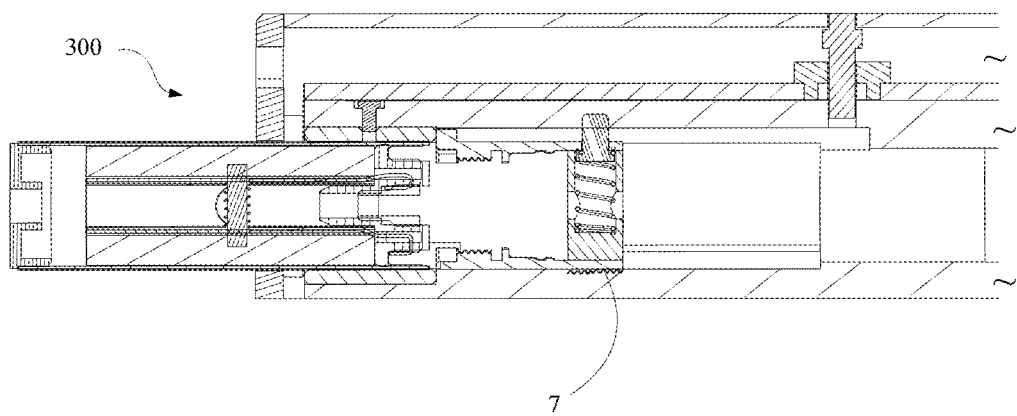
FIG. 4 is a schematic partial cross-section view of an electronic cigarette in a first state according to a third embodiment of the present disclosure.

FIG. 4 illustrates an electronic cigarette 300 according to a third embodiment of the present disclosure. The electronic cigarette 300 shown in FIG. 4 is similar to the electronic cigarette 100 shown in FIGS. 1 and 2, except that the electronic cigarette 300 further includes an outer thread 7 arranged on the other end of the atomizer 2 opposite to the mouthpiece 21; an inner thread (not shown) is arranged in the sleeve 1 at the second limiting position and configured to engage with the outer thread 7, such that the outer thread 7 engages with the inner thread to fix the atomizer 2 to the sleeve 1 when the other end of the atomizer 2 opposite to the mouthpiece 21 is pushed outwards to the second limiting position by applying an external force.

Described above are exemplary embodiments of the present disclosure, but are not intended to limit the scope of the present disclosure. Any equivalent structure or equivalent process variation made based on the specification and drawings of the present disclosure, which is directly or indirectly applied in other related technical fields, fall within the scope of the present disclosure.

What is claimed is:

1. An electronic cigarette, comprising:
   a housing;
   a sleeve received in the housing, the sleeve comprising a first limiting position and a second limiting position, the sleeve defining a positioning hole on an inner wall thereof, the positioning hole arranged at the first limiting position;
   an atomizer comprising a mouthpiece, the atomizer capable of being inserted into the sleeve and telescoping relative to the sleeve along an axial direction of the sleeve, so as to expose the mouthpiece or take out the atomizer from the sleeve;
   a latch assembly arranged on an end of the atomizer opposite to the mouthpiece, the latch assembly configured to latch the atomizer in the sleeve when the atomizer is retracted into the sleeve and is positioned at the first limiting position, the latch assembly comprising a first elastic assembly and a limiting pin, and the first elastic assembly elastically offsetting the limiting pin along a radial direction of the sleeve, such that when the end of the atomizer opposite to the mouthpiece is retracted in the first limiting position, the limiting pin is aligned with the positioning hole and is latched in the positioning hole; and
   a control assembly arranged on the sleeve, the control assembly configured to unlock the latch assembly to allow the end of the atomizer to move to the second limiting position along the axial direction of the sleeve.

2. The electronic cigarette according to claim 1, further comprising a second elastic assembly, wherein an end of the second elastic assembly abuts against the end of the atomizer opposite to the mouthpiece, the other end of the second elastic assembly is connected to a bottom of the sleeve, and the second elastic assembly is capable of pushing the atomizer outwards along the axial direction of the sleeve when the atomizer is retracted in the sleeve.

3. The electronic cigarette according to claim 2, wherein both the first elastic assembly and the second elastic assembly are springs.

4. The electronic cigarette according to claim 1, wherein the control assembly comprises a control button, the control button is arranged on the first limiting position and partially exposed on an outer side of the sleeve, such that the limiting pin is capable of being unlocked from the first limiting position by pressing the control button.

5. The electronic cigarette according to claim 4, wherein the second limiting position is arranged on the inner wall of the sleeve and is spaced apart from the first limiting position at a predetermined distance.

6. The electronic cigarette according to claim 4, wherein the sleeve defines an axial limiting groove in the inner wall thereof, the axial limiting groove is communicated with the positioning hole, and the axial limiting groove is configured to receive and guide the limiting pin when the atomizer telescopes relative to the sleeve along the axial direction of the sleeve.

7. The electronic cigarette according to claim 1, further comprising an air pump; wherein the air pump is arranged on a bottom of the sleeve and capable of pushing the atomizer outwards along the axial direction of the sleeve when the atomizer is retracted in the sleeve.

8. The electronic cigarette according to claim 1, further comprising an outer thread arranged on the end of the atomizer opposite to the mouthpiece; wherein the sleeve defines an inner thread configured to engage with the outer thread, the inner thread is arranged at the second limiting position, such that the outer thread engages with the inner thread to fix the atomizer to the sleeve when the end of the atomizer opposite to the mouthpiece is pushed outwards to the second limiting position.

9. The electronic cigarette according to claim 1, wherein the latch assembly is configured to latch the atomizer in the sleeve when the atomizer is retracted at the first limiting position and an outer end portion of the mouthpiece is flushed with an outer end portion of the housing.

* * * * *